United States Patent [19]

Monguzzi et al.

[11] 4,231,927
[45] Nov. 4, 1980

[54] HYDRAZONO PENICILLIN DERIVATIVES

[75] Inventors: Riccardo Monguzzi; Giorgio Pifferi; Mario Pinza; Giampietro Broccali, all of Milan, Italy

[73] Assignee: CRAF Sud, Aprilia Latina, Italy

[21] Appl. No.: 913,325

[22] Filed: Jun. 7, 1978

[30] Foreign Application Priority Data

Jun. 7, 1977 [IT] Italy ............................. 24337 A/77

[51] Int. Cl.$^3$ ................. C07D 499/68; C07D 499/70
[52] U.S. Cl. ................................. 260/239.1; 424/271
[58] Field of Search ....................................... 260/239.1

[56] References Cited

U.S. PATENT DOCUMENTS 3,926,957  12/1975  Gregson et al. ................. 260/239.1

OTHER PUBLICATIONS

Ekstrom et al., Acta Chemica Scandinavica, 19, pp. 281-299, (1965).
Moses et al., Arkiv För Kemi 22, (33), pp. 451-467, (1964).

Primary Examiner—Natalie Trousof
Assistant Examiner—Vera C. Clarke
Attorney, Agent, or Firm—Stevens, Davis, Miller & Mosher

[57] ABSTRACT

Hydrazono penicillin derivatives of the formula

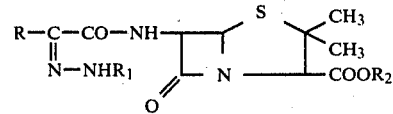

wherein R represents phenyl optionally substituted, 2- or 3- thienyl optionally substituted, or 2- or 3- furyl optionally substituted, $R_1$ represents hydrogen, alkyl containing from 1 to 4 carbon atoms, or phenyl, and $R_2$ represents hydrogen, pivaloyloxymethyl, or 1-(ethoxycarbonyloxy)ethyl radical. The compounds have antibacterial activity against gram-negative and gram-positive microorganisms. Methods of preparation are also disclosed.

7 Claims, No Drawings

HYDRAZONO PENICILLIN DERIVATIVES

The present invention relates to new hydrazono penicillin derivatives having a high antibiotic activity and to the preparation thereof.

More particularly the hydrazono derivatives of the present invention have the structural formula

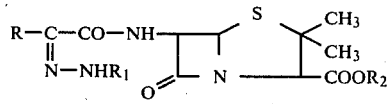

wherein

R represents phenyl optionally substituted, 2- or 3-thienyl optionally substituted, or 2- or 3-furyl optionally substituted, $R_1$ represents hydrogen, alkyl containing from 1 to 4 carbon atoms, or phenyl and, $R_2$ represents hydrogen, pivaloyloxymethyl or, 1-(ethoxycarbonyloxy)ethyl radical Compounds of formula I may be, depending upon the planar structure of the hydrazono group, in the Z (sin) or E (anti-) form or as a mixture of the forms Z and E.

The present invention further comprises the pharmacologically acceptable salts of compounds of formula I with alkali or alkaline-earth metals and with suitable organic bases. Among the alkali and alkaline-earth metals the sodium and potassium salts are the preferred and among the organic bases the amines such as procaine, N,N-dibenzylethylendiamine and dibenzylamine are preferred.

According to the present invention compounds of formula I, wherein $R_2$ represents a pivaloyloxymethyl and 1-(ethoxycarbonyloxy)ethyl radical, are prepared by condensing 6-aminopenicillanic acid suitably protected at the carboxylic group, with a protected derivative of α-hydrazo-noacetic acid previously treated with 2,4-dinitrophenol and subsequently removing the protecting group at the hydrazonic nitrogen by catalytic hydrogenolysis. Compounds of formula I wherein $R_2$ is hydrogen are obtained according to known techniques. The protected derivatives of α-hydrazonoacetic acid are themselves new and may be suitably prepared starting from a suitable glyoxylic acid derivative by reaction with a hydrazine derivative and subsequent introduction of the protecting group at the hydrazonic nitrogen. As an alternative these compounds may be obtained by reacting the starting glyoxylic acid derivative with a previously protected hydrazine derivative. The process may be schematically represented as follows

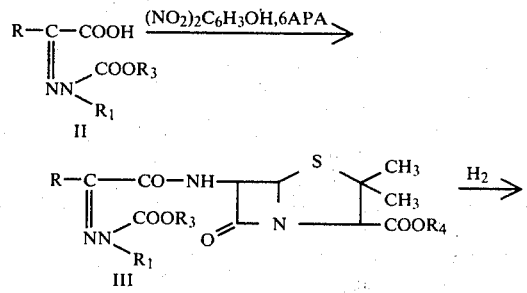

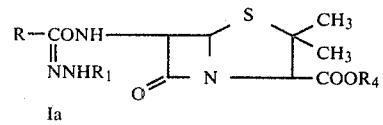

wherein R and $R_1$ have the above meaning, $R_3$ represents a benzyl radical and suitable similar protecting groups and $R_4$ represents pivaloyloxymethyl or, 1-(ethoxicarbonyloxy)ethyl radical.

Compounds III and Ia, wherein $R_4$ is represented by benzyl, benzhydryl radical and other suitable protecting groups, are also comprised in the present invention.

More particularly α-hydrazonoacetic acid in protected form II is reacted with 2,4-dinitrophenol in the presence of a dehydrating agent in an aprotic solvent and then condensed with 6-aminopenicillanic acid protected at the carboxyl group. Cyclic ethers such as dioxane and tetrahydrofuran or acetonitrile are suitable solvents: dicyclohexylcarbodiimide is the dehydrating agent generally used, but other similar compounds may be employed and particularly ethoxyacetylene. The condensing reaction is conducted preferably in the presence of an organic base such as a tertiary amine at a temperature between $-5°$ C. and room temperature. Afterwards the protecting group is removed by catalytic hydrogenation from the hydrazonic nitrogen and, if necessary and convenient, the compound Ia is hydrogenized to give derivatives I wherein $R_2$ is represented by an hydrogen atom.

As an alternative the condensing reaction between the α-hydrazonoacetic acid derivative in protected form II and 6-aminopenicillanic acid protected at the carboxyl group as ether or suitable salt, for obtaining compounds of formula I wherein $R_1$ is not represented by hydrogen is conducted by treatment with ethyl chlorocarbonate in the presence of catalytic quantities of a tertiary base in an aprotic solvent at a temperature between $-40°$ and $10°$ C. As an alternative to ethyl chlorocarbonate, allyl chlorocarbonate or di isobutyl may be employed and as a tertiary base dimethylpiperazine, ethylpiperidine and methylmorpholine may be employed. Chlorinated hydrocarbons are the more suitable aprotic solvents, among which methylene chloride and chloroform are preferred.

As an alternative to the process of the present invention, compounds of formula I wherein $R_1$ is not hydrogen and, preferably is phenyl, may be prepared by direct condensation of α-hydrazonoacetic acid derivative with 6-aminopenicillanic acid protected at the carboxyl group in the form of an ester or salt, in the presence of a suitable dehydrating agent such as dicyclohexylcarbodiimide preferably. The reaction occurs at room temperature in an aprotic solvent preferably formed by cyclic ethers such as tetrahydrofuran and dioxane and may be schematically represented as follows:

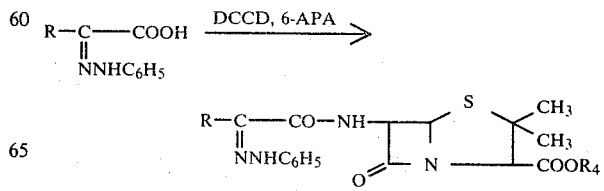

wherein R and $R_4$ have the above meanings.

Compounds of formula I have antibacterial activity especially against gram-positive microorganisms including some penicillinase-producers. They are also valuably active against gram-negative microorganisms. In comparison with ampicillin, the products of the invention are more active against some gram-positive penicillinase-producer microorganisms (Staphylococcus aureus). The minimum inhibiting concentration (MIC) in vitro of the compounds of the present invention has been evaluated for some microorganisms, expressed in γ/ml and compared with that of 6-(α-methoxyiminophenylacetamide)-penicillanic acid which has—among the known compounds—the closest chemical structure and belongs to the class of penicillanic acid derivatives described in British Pat. No. 1,399,087.

The compounds of the invention when compared to the standard have a similar activity against gram-negative microorganisms, but are considerably more active against gram-positive microorganisms.

The experimental results obtained are shown in the following Table. All the products of the invention are resistant to acids and do not lose their biological activity even after treatment for one hour with hydrochloric acid N/20.

stirring for one hour and after evaporation under vacuo a precipitate is collected, consisting of 35 g α-(N-benzyloxy-carbonyl-N-methylhydrazono)phenylacetic acid sodium salt as monohydrate melting at 166°–168° C. (with decomposition). By dehydration through azeotropic distillation with benzol, the anhydrous form is obtained.

To a suspension consisting of 5.59 g anhydrous α-(N-benzyloxy-carbonyl-N-methylhydrazono)phenylacetic acid sodium salt in 80 ml methylene chloride containing 0.4 ml N-methylmorpholine, 1.8 ml ethyl chlorocarbonate is added under stirring at −35° C. The mixture is kept under stirring at −35° C. for one hour and 11 g 6-aminopenicillanic acid triethylamine salt diluted in 80 ml methylene chloride are added thereto. The temperature is raised to 0° C. and then the solvent is evaporated under vacuo. The residue is taken up with 50 ml ethyl acetate and 50 ml water and acidified in the cold to pH 1. The organic phase, washed with water and made anhydrous, is evaporated under vacuo and the oily residue, treated with 6.8 ml isopropyl alcohol solution of sodium ethylhexanoate and with isopropyl ether, gives 5.2 g 6-[α-benzoxycarbonyl-N-methylhydrazono)phenylacetamido]penicillanic acid sodium salt as white solid melting at 161°–162° C. (with decomposi-

|  | 6-(α-methoxyiminophenylacetamido)penicillanic acid | 6-(α-methylhydrazonophenylacetamido)sodium penicillanate | pivaloyloxymethylester of 6-(α-hydrazonophenylacetamido)penicillanic acid |
|---|---|---|---|
| Staphylococcus aureus pen. - sens. str. 1 | 0.097 | 0.39 | 0.19 |
| Staphylococcus aureus pen. - sens. str. 2 | 0.19 | 0.39 | 0.097 |
| Staphylococcus aureus pen. - res. str. 3 | 6.25 | 6.25 | 3.12 |
| Staphylococcus aureus pen. - res. str. 4 | 3.12 | 1.56 | 0.78 |
| Staphylococcus pyogenes | 0.78 | 0.19 | 0.048 |
| Diplococcus pneumoniae | 0.78 | 0.19 | 0.048 |
| Sarcina lutea | 0.012 | 0.097 | 0.012 |
| Bacillus subtilis | 0.048 | 0.097 | 0.012 |
| Escherichia coli | 100 | 12.5 | 25 |
| Shigella dysenteriae | 50 | 12.5 | 25 |
| Salmonella typhi | >200 | 12.5 | 25 |
| Salmonella typhimurium | >200 | 12.5 | 25 |
| Pseudomonas aeruginosa | >200 | >200 | >200 |

EXAMPLE 1

6-(α-Methylhydrazonophenylacetamido)penicillanic acid sodium salt

Six grams of phenylglyoxylic acid are diluted in 200 ml methylene chloride and 43 ml methylhydrazine are added thereto.

The mixture is stirred at room temperature for one hour and a half and then it is extracted with 200 ml of 2 M sodium hydrate solution. The aqueous solution is then acidified at pH 2 in the presence of 200 ml methylene chloride. The organic phase is separated, made anhydrous and concentrated under vacuo. The residue oil, slurried from isopropyl ether, gives 3.6 α-methylhydrazonophenylacetic acid melting at 117°–121° C. (with decomposition).

A suspension consisting of 18 g α-methylhydrazonophenylacetic acid in 180 ml water is treated with 102 ml of M sodium hydrate solution and then with 180 ml dioxane. To the so obtained solution cooled to 5° C., under stirring, 17.2 ml benzyl chlorocarbonate diluted in 200 ml dioxane and 14 g sodium carbonate diluted in 200 ml water are meanwhile dropwise added. After tion).

A stream of hydrogen is bubbled into a solution of 2.5 g 6-[α-(N-benzoxycarbonyl-N-methylhydrazono)-phenylacetamido]penicillanic acid sodium salt in 15 ml ethyl alcohol and 5 ml water containing 1 g 10% palladium on charcoal. It is filtered over celite and the filtrate is evaporated under vacuo. The residue, slurried with acetone and isopropyl ether, gives 1 g 6-(αmethyl-hydrazonophenylacetamide)penicillanic acid sodium salt as white crystals, melting at 187°–190° C. (with decomposition).

EXAMPLE 2

Pivaloyloxymethyl ester 6-(α-methylhydrazonophenylacetamido)penicillanic acid.

1.86 grams anhydrous α-(N-benzoxycarbonyl-N-methylhydrazono)phenyl-acetic acid sodium salt obtained as described in the previous Example, are suspended in 40 ml methylene chloride containing 3 drops of N-methylmorpholine, and 0.58 ml ethyl chlorocarbonate are added thereto under stirring at −35° C. It is kept under stirring at −35° C. for one hour and then 1.68 g pivaloyloxymethyl ester of 6-aminopenicillanic acid diluted in 30 ml methylene chloride are added thereto. The temperature is brought to 0° C. and thereafter the material is extracted with an aqueous solution of sodium bicarbonate, then with 10% hydrochloric acid and finally with water. The organic phase, evaporated under vacuo, gives and oil which, by treatment with methyl alcohol solidifies, and 0.7 g pivaloyloxymethyl ester of 6-[α-(N-benzoxycarbonyl-N-methylhydrazono)phenylacetamido]penicillanic acid, as white solid melting at 104°–105° C., are obtained. To a solution of 2.05 g pivaloyloxymethyl ester of 6-[α-(N-benzoxycarbonyl-N-methylhydrazono)phenylacetamido]-penicillanic acid in 50 ml ethyl alcohol, 2 g 10% palladium on charcoal are added, and into the mixture a stream of hydrogen is bubbled until the development of carbon dioxide ends. The solution is evaporated under vacuo at room temperature and by slurrying from petroleum ether, 0.26 g pivaloyloxymethyl ester of 6-(α-methylhydrazonophenylacetamido)penicillanic acid melting at 85°–88° C. (with decomposition) are obtained. Operating as above described and using as the starting material furylglyoxylic acid, pivaloyloxymethyl ester of 6-(α-methylhydrazonofurylacetamido)penicillanic acid is prepared and using ethoxycarbonyloxy-1-ethyl ester of 6-aminopenicillanic acid, ethoxycarbonyloxy-1-ethyl ester of 6-(α-methylhydrazonophenylacetamido) penicillanic acid is obtained.

EXAMPLE 3

Pivaloyloxymethyl ester of (Z) 6(α-hydrazonophenylacetamido)penicillanic acid

To a solution of 3.6 g phenylglyoxylic acid in 47 ml ethyl acetate 4g benzoxycarbonylhydrazine are added. The mixture is kept under stirring for one hour, then filtered under vacuo separating the mother liquors and 2.35 g α-benzoxycarbonylhydrazonophenylacetic acid (Z) as white crystals, melting at 159°–160° C., are obtained. 1.38 grams of dicycloexylcarbodiimide are added to a solution of 2 g α-benzoxycarbonylhydrazonophenylacetic acid (Z) and of 2,4-dinitrophenol, in 20 ml tetrahydrofuran, and then kept under stirring for one hour. (Mixture A).

At the same time 2.46 g pivaloyloxymethyl ester of 6-aminopenicillanic acid hydrochloride in 40 ml tetrahydrofuran are treated at 0° C. with 0.92 ml N,N'dimethylpiperazine (Mixture B) and, after 20 minutes the mixture B is poured into the mixture A; the mixture is allowed to stand under stirring overnight, then filtered under vacuo and, the filtrate concentrated under vacuo at room temperature. The residue dissolved in ether is washed with a sodium bicarbonate solution, diluted hydrochloric acid and water. The solvent is made anhydrous and evaporated and 3.31 g pivaloyloxymethyl ester of 6-[α(N-benzoxycarbonylhydrazono)-phenylacetamido]penicillanic acid (Z), as an oil, are obtained; Rf 0.16 (silica gel—eluent hexane:ethyl acetate 7:3). 2 grams of 10% palladium on charcoal are added to a solution of 2.35 g pivaloyloxymethyl ester of 6-[αN-benzoxycarbonylhydrazono)pheylacetamido]-penicillanic acid (Z) in 50 ml ethyl alcohol and a stream of hydrogen is bubbled into the mixture.

The catalyst is removed, the solution is evaporated under vacuo to dryness, the residue is slurried from petroleum ether, and 0.36 g pivaloyloxymethyl ester of 6-(α-hydrazonophenylacetamido)penicillanic acid (Z) are obtained, having an amorphous appearance and yellow colour and melting at 65°–67° C. Operating as above described 6-(α-methylhydrazonophenylacetamido) penicillanic acid sodium salt, pivaloyloxymethyl ester of 6-(α-methylhydrazonophenylacetamido)penicillanic acid, pivaloyloxymethyl ester of 6-(α-methylhydrazonofurylacetamido)penicillanic acid, ethoxycarboniloxy-1-ethyl ester of 6-(α-methylhydrazonophenylacetic)penicillanic acid and pivaloyloxymethyl ester of 6-(α-phenylhydrazonophenylacetamido)penicillanic acid are prepared.

EXAMPLE 4

Pivaloyloxymethyl ester of 6-(α-hydrazonophenylacetamido)penicillanic acid (E)

Mother liquors obtained by filtration of α-benzoxycarbonylhydrazonophenylacetic acid (Z) are evaporated to dryness under vacuo and the residue is slurried from ether and filtered to give 3 g of white crystals of α-benzoxycarbonylhydrazonophenylacetic acid (E) (m.p. 156°–158° C.) from which, operating as above described in the previous Example, pivaloyloxymethyl ester of 6-(α-hydrazonophenylacetamido)penicillanic acid (E) is obtained.

EXAMPLE 5

Pivaloyloxymethyl ester of 6-(α-phenylhydrazonophenylacetamido)penicillanic acid A suspension of 7.6 g pivaloyloxymethyl ester of 6-aminopenicillanic acid hydrochloride in 100 ml tetrahydrofuran is treated at 0° C. with 2.95 ml triethylamine and is kept under stirring for 20 minutes. Then 4.34 g dicyclohexylcarbodiimide and subsequently 4.81 g α-phenylhydrazonophenylacetic acid dissolved in 25 ml tetrahydrofuran are added thereto. The mixture is kept under stirring at 0° C. for 1 hour, filtered under vacuo, the filtrate concentrated to dryness at room temperature under vacuo, the residue dissolved in ethyl alcohol and the product precipitated by addition of water. 3.63 grams of pivaloyloxymethyl ester of 6-(α-phenylhydrazonophenylacetamido)penicillanic acid of yellow colour, melting at 70°–74° C. are obtained.

We claim:

1. Hydrazono penicillin of the formula

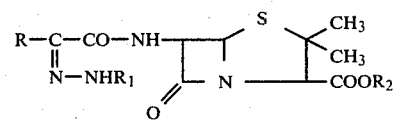

wherein R represents phenyl, 2- or 3- thienyl or 2- or 3-furyl, $R_1$ represents hydrogen or alkyl containing from 1 to 4 carbon atoms, $R_2$ represents hydrogen, sodium, potassium, pivaloyloxymethyl or 1-(ethoxycarbonyloxy)-ethyl, in separated form E or Z or mixture of the same.

2. 6-(α-Methylhydrazonophenylacetamido)penicillanic acid sodium salt.

3. Pivaloyloxymethyl ester of 6-(α-methylhydrazonophenylacetamido)penicillanic acid.

4. Pivaloyloxymethyl ester of 6-(α-methylhydrazonofurylacetamido)penicillanic acid.

5. Ethoxycarbonyloxy-1-ethyl ester of 6-(α-methylhydrazonophenylacetamido)penicillanic acid.

6. Pivaloyloxymethyl ester of 6-(α-hydrazonophenylacetamido)penicillanic acid (Z).

7. Pivaloyloxymethyl ester of 6-(α-hydrazonophenylacetamido)penicillanic acid (E).

* * * * *

UNITED STATES PATENT AND TRADEMARK OFFICE
CERTIFICATE OF CORRECTION

PATENT NO. : 4,231,927

DATED : November 4, 1980

INVENTOR(S) : Riccardo Monguzzi; Giorgio Pifferi; Mario Pinza; Giampietro Broccali It is certified that error appears in the above-identified patent and that said Letters Patent are hereby corrected as shown below:

IN THE SPECIFICATION:

Column 1, line 42, change "α-hydrazo-noacetic" to -- α-hydrazonoacetic --.

Column 5, line 7, change "gives and oil" to -- gives an oil --.

Signed and Sealed this

Nineteenth Day of May 1981

[SEAL]

Attest:

RENE D. TEGTMEYER

Attesting Officer     Acting Commissioner of Patents and Trademarks